United States Patent
Keshi et al.

(10) Patent No.: US 6,172,215 B1
(45) Date of Patent: Jan. 9, 2001

(54) PROBES FOR DETECTING AND IDENTIFYING *HELICOBACTER PYLORI*

(75) Inventors: Hiroyuki Keshi, Osaka; Soji Eda, Kyoto; Hirotsugu Uehara, Takarazuka; Keigo Nishida, Higashi-Osaka; Akio Matsuhisa, Osaka, all of (JP)

(73) Assignee: Fuso Pharmaceutical Industries, Ltd., Osaka (JP)

( * ) Notice: Under 35 U.S.C. 154(b), the term of this patent shall be extended for 0 days.

(21) Appl. No.: 09/230,380

(22) PCT Filed: Jul. 24, 1997

(86) PCT No.: PCT/JP97/02552

§ 371 Date: Jul. 12, 1999

§ 102(e) Date: Jul. 12, 1999

(87) PCT Pub. No.: WO98/03681

PCT Pub. Date: Jan. 29, 1998

(30) Foreign Application Priority Data

Jul. 24, 1996 (JP) .................................. 8-194317

(51) Int. Cl.⁷ .................................. C07H 21/04
(52) U.S. Cl. .................. 536/24.32; 536/23.1; 536/24.33; 435/6
(58) Field of Search ............................. 536/24.32, 23.1, 536/24.33; 435/6

(56) References Cited

PUBLICATIONS

Database GenBank Rel. 100, National Center for Biotechnology Information, Accession U75328, Jan. 2, 1997.
Database GenBank Rel. 100. National Center for Biotechnology Information, Accession U86610, Feb. 13, 1997.
Desai et al., "Genetic diversity of *Helicobacter pylori* indexed with respect to clinical symptomology, using a 16S rRNA and a species–specific DNA probe" *J. Applied Bacteriology* vol. 75, pp. 574–582 (1993).
Li et al., "A Highly Specific and Sensitive DNA Probe Derived from Chromosomal DNA of *Helicobacter pylori* Is Useful for Typing *H. pylori* Isolates" *J. Clinical Microbiology* vol. 31, pp. 2157–2162 (Aug. 1993).

*Primary Examiner*—Jeffrey Fredman
*Assistant Examiner*—Juliet C. Einsmann
(74) *Attorney, Agent, or Firm*—Marshall, O'Toole, Gerstein, Murray & Borun (57) ABSTRACT

DNA probes for detecting the presence of *Helicobacter pylori* are provided. These isolated, purified oligonucleotide probes are useful in assays for the specific detection of *Helicobacter pylori* because they specifically hybridize to the DNA of *H. pylori*.

1 Claim, 2 Drawing Sheets

Strain No. of blotted strain DNA

| 1 | 9  | 17 |
|---|----|----|
| 2 | 10 | 18 |
| 3 | 11 | 19 |
| 4 | 12 | 20 |
| 5 | 13 | 21 |
| 6 | 14 | 22 |
| 7 | 15 | 23 |
| 8 | 16 | 24 |

SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthesized DNA

<400> SEQUENCE: 1
cgacgttgta aaacgacggc cagt                                          24

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthesized DNA

<400> SEQUENCE: 2
caggaaacag ctatgac                                                  17

<210> SEQ ID NO 3
<211> LENGTH: 1778
<212> TYPE: DNA
<213> ORGANISM: Helicobacter pylori
<220> FEATURE:
<223> OTHER INFORMATION: At position 1529, n = any nucleotide (g, a, c or t)

<400> SEQUENCE: 3
aagcttctag taaagaaatc actcttttt gctgttccaa tagtgcgtct atcttggcac      60
tcaaacgatt tattttactt tccatgcgtt caatactaac cactaaaaat aaatagctat    120
ttaatcatta aaaatgatta ttttaatacc atgctcttaa attaagatgt gtttttatga    180
tcatgctaca ataaaaacac aaaatgattt caaagaaaaa gggtttaaaa tgaaaacttt    240
tgaagtaatg attcaaaccg attcaaaagg gtatttggac gctaaatttg gcggtacgct    300
cctagagggt ttctcaatcc aaacggctta cccacttatt cgcctaaaat ctcatggcaa    360
aaagtagaag gcgctcaaag ctatgcacta gaactcatcg atcatgacgc tcaaaaagtg    420
tgtggcatgt cgtttgtcat tgggtcgtgg gcaatatttc ttataatgtt ttagaagaaa    480
acgcttccat gatggataaa agaattgttc aagggtcaa ttcgctcact caaggcttta    540
tccgttcccc acttaatgaa agcgaaaaac aacgctccaa tctcaataac agcacctata    600
tcggccccat gccccctaat ggcgatcacc attacttaat ccaagtgtat gccctagaca    660
ttcctaaact cgccttaaaa gccccgtttt tcttaggcga tttgcatgac agaatgcgcg    720

```
gacatatcat cgccataggg agaaaagaat ttttatacaa gcagtttgtg aggaaatagg      780
ctactgcttg tagctattct ttcgctaaat tgaattttttg atacatctct aaaattctct     840
tttcatctag catgctttct tcaatccttg tgcctatcaa atcggcatgg tgcttttttaa     900 aatcttttaa agggattaaa tcattatcaa caagagcgtt tcgcctcttt ttagctaaag      960
ggaagtgcca ttgcacgagt tctttatcct taaatatggt gtttatcctt aagccttaaa    1020
gttttataag catcaccatt atattgccaa atttcaaaag gctcacaatc gttataaaat    1080
aaccaatgat ctccccatgc gtctaaaaat ccaaaatccc catcattacg cataaacacc    1140
tcaaaatctt gcaccacaaa attaatacgc gaatacatca caacctcttt aatgctctta    1200
gggatataaa aactttcata agttttttta gcgtcataaa tatgatcaca atcaattttg    1260
ataacccact cattttttagg gataaaagaa agcgtataat tatagtaatg atagagttgg    1320
tgccacaaac tcgggcaatc ctttagtatg acttcataag gatagctgat agggataaat    1380
gaggggaact ttttacaaaa ctctaaaatc acttctttag agccatcatc gcaatcatta    1440
aaaccaatga ccccccttttg aatggcagga agcatagaaa acaaactctc ttctaaagta    1500
acgatttcat ttttgactct aataaaagnc catgggttta gagggctttt agggttttga    1560
cttttttatc atagtcaaaa taacctgaat gcgtgggatt gggtagagtt aaagtgggat    1620 ggataacccct atcttctaaa tgcccccccc cccccataa ttataattaa gagaactatt     1680
tttataaata ctcttattgc gttcaatgaa actttcatta tttaaagaag cgatagccaa    1740
aaacacgctt tcttgatggt catggttgaa taaagctt                             1778

<210> SEQ ID NO 4
<211> LENGTH: 1426
<212> TYPE: DNA
<213> ORGANISM: Helicobacter pylori

<400> SEQUENCE: 4
aagctttacc tctaatagcg tttttaaactt ttttgtggtt ttgtctttca tcacgatagg     60
gctagttttt ttcttttttgc gttcccaacc cactagcgtg gtctctaaag aaaatattcc   120
taaaattgaa ttagaaaatt ttaaagcgtt tcaaatcaac gataaaatcc ttgatctgtc    180
catagagggc aaaaaagctc tacaatacga tgatcatgag atctttttttg attccaaaat   240 caagcgttat gatgaagaca cgatagaaag cgttgaatcc cctaaagcca acggcagca    300 ggatttgtat ttcttcccta atggggtaac ttataaaaga agcgatgatt ctagttttttg   360 gagtgaaaca gggatttaca accataagga gcaaaatttt aaaggcaagg gccgtttcat   420
tctcactcaa aggacagcaa ggttgaaggg cttgacattt cttattcgca tgcttttagcc   480 attattgaag cccaaagcat tcaagctaat ttattcttag atgaaatcaa acaaagccag    540
aaagaaaaga aaaattccc cactttcaaa ggagggtttt taatgcgttg gtggtgtgtt     600
cttgtgtgtt gttttggaat ttaagcgtg atgaacgctc aaaaaacaga caataaaggt     660
ttgaaaaaag aaagagaaac ttttagaaat taccggcaac aaattcgtag cgaacgacaa    720
aacaaaaacc gccgttattc aaggcaatgt gcagatcaaa aaggtaaag accggttgtt    780 tgcggataag gtgagcgtgt ttttaaacga taaacgaaag ccagagcgct atgaagccac   840
agggaacacg cattttaaca tctttacaga ggataatcgt gaaatcagcg ggagtgctga   900
caagctcatt tataacgcac tgaatgggga atacaaatta ttgcaaaatg cggtggttag   960
agaagtgggg aaatctaatg ttattaccgg tgatgagatc attttaaaca aagctaaggg  1020
```

-continued

```
ttatgctgat gtgttgggga gcacgaaacg gcccgctaaa tttgtgtttg atatggaaga      1080
cattaatgaa gaaatcgta aggccaaatt gaagaagaaa ggcgctaagg aaaaaccatg      1140
atcgctatta aagacgctca ttttctcact tcttctagcc aactttcgca atgccctgcg      1200
agcttgactt ctgaaatggt cattttaggg cgcagcaatg tcggtaaaag ctcgtttatt      1260
aataccttgt taggaaaaaa tctcgctaaa agttcagcaa cgcctggaaa acccgttta      1320 gtgaattttt tttccaccac ttgggaagat aaagaaaacg ccttaagggc cacttttaat      1380
gtgattgatt tgcctgggtt tgctacgcta agtttctaa aagctt                     1426
```

<210> SEQ ID NO 5
<211> LENGTH: 723
<212> TYPE: DNA
<213> ORGANISM: Helicobacter pylori

<400> SEQUENCE: 5

```
aagctttgcc aactttacca acacaacaaa gatttagtag caagtatatg attttggtca      60
aatcaaatga gttatactat gcaataggta gtgctattaa tcaagattta agctcttctc     120
ctatcttcaa aacaaatgtt tccccaaaca aattgatgct gtataaaaat ggaaaaattt     180
catctatgat caaggagaa aaggggtttg ggggtcatga aggttctgag atagtagatg      240
ctactgagct agctacagga tttatgaacc acattgtccc tattcttagt tataaactag      300
attgtccata ttcttaatta taaactagcg gaaatctatt atgaagcata tgtcgaaact     360
aatcgtcttt taacgaaaat caaggctac tcgcacaaca aaacactttt gttacccaac     420
aaattaatgc cttaaaagct aaactaaat ttctccaaaa agtttataag gatatttctc      480
aaatttctaa aagtgatgtt tgatacaat caacatgcac aaatttacaa agaatacgca     540
ttgaactaga tgaaattttt tataatttta tatcccaaat aaatcaagga ctaatggtaa     600
aaaactttaa tgatgtaagt ggtaactaca tttgtgcaag atacgctctt tctcattata     660
tttttgcgtt ggttttagaa tatgttgttg caggactcat tgataatgag agcatggaag     720
ctt                                                                    723
```

<210> SEQ ID NO 6
<211> LENGTH: 339
<212> TYPE: DNA
<213> ORGANISM: Helicobacter pylori

<400> SEQUENCE: 6

```
aagcttttgc ctggcacggc tatgcctaga gtggggttga gcgaacaggc tcaaaaacaa      60
gtcatcgcat atttggaaaa agcgggcgat aggaaaaaac atgaaaggaa cacttaggg     120 ataaaaatca tgatttctt tgcggtgctg tcgttcttgg cttatgcgtg gaaagaaag     180 gtttggagcg aagtgcattg aattaaaaaa aggggaggg catggtttta tgattttga      240 tctatggtgg ggtgtttgaa tggcgttttc aaaacaacct ttattttagg atttttattat   300 tactaatacc cctataagga ttttatggct acaaagctt                            339
```

<210> SEQ ID NO 7
<211> LENGTH: 925
<212> TYPE: DNA
<213> ORGANISM: Helicobacter pylori

<400> SEQUENCE: 7

```
aagcttgaaa tattaatgct tcaaatgagt ttggtttaat ctttaattaa agaaaaagtc      60
atcaaactag cccaaacatt aggaatcaac atgatcattg gcgggcctcc ctgtcaaggc     120
```

```
ttttctaata aagggaaaaa tttagggcta aaagactcta ggaatttttt atttttagaa      180
tatatagaga tagtaaaagc cttaaaacca gaaatttta tcattaaaaa catgaaaaac       240
ctcatctctt gcgctaaagg ctattttta gaagaaatta agaaagatt gaacgcttta        300 gggtatcaat taagctatca aatcctaaat gctaaagatt atggcgtgcc tcaaaacaga      360
gagagggcct ttattgtggg ggctagtcgt tttagttttg atttcaatct tttagagcct     420
tctcaaagcg tgaatgttca ggatgcgata agcgatttag cctatcttgt tctaatgagg    480
gggcgtttga aagcgattat ttaaacccta tccaatcaag ctatcaagcc ttgatgcgaa     540
aagatagccc taaattatac aaccatcaag ccaccaacca ctcgcaagcc gctttagaga    600
aattaaagct cattaacaaa gagcaaggca agaatgctt gcctaaaaac ttgcatggca     660
aacagcaatt caaagcaca tggggcgtt tgaattggaa taaaatcagc cccaccatag      720 acacgatt tgacactcca gtaatggca ccaactccca cctgaattg caccgctcta       780 tcacgcccag agaagccgct aggatacaaa gttttagcga taattatatc ttttatggca    840
ataaaacgag cgtttgcaag caatcggta acgctgtgcc cctcttcta gccctagctt      900 taggcaaagc gatcttaaaa agctt                                            925

<210> SEQ ID NO 8
<211> LENGTH: 2393
<212> TYPE: DNA
<213> ORGANISM: Helicobacter pylori

<400> SEQUENCE: 8
aagcttgaag gtgcgttaaa atgaaaatct ctttatttgg gcatggcaaa accactctag    60
ccttagggcg ttttttttaga aaaaaccata acgaagtcaa atttttgac gaccaattca     120 ctgcatcttt taaagatagc gagggttttg tttgctatcc cagtaaggat ttcaacccta    180
atgattccca actagagata gtcagccctg gcattagctt cacgcaccct ttagtcataa    240
aagccaagca tttagtgagc gaatacgatt atattgatag cttgtttgat ttggttttca    300
cgcctactat aataagtatt agcggcacta atggtaaaac caccacgaca gaaatgctca    360
ccatgctttt agaagatttt aaggctgtga atggggggaa tatcggcacg cccttgattg    420
aattgtttga aaaacaatcg cccttgtggg tgttagaaac aagctccttt tctttgcatt    480
acactaataa ggcttaccct ttaatctact tgctcatcaa tgtggaagct gatcatttga    540
cttggcattg caattttgaa aattatttga acgctaaact caaggttta acattgatgc     600 ctaaaacttc actcgctatc ctcccttaa aattcaaaga acattcaagc gttcaaaatt    660
cgcaagcgca aaaaatcttt tttgacaaaa gcgaagaggt tttagagcgt ttaaaaatcc    720
cttctaacgc cctttttttt aaaggagcgt ttttattaga cgctgcatta gccctttag     780 tttacgagca attttaaaa ataagaatt taaaatggca agattataga gaaaacgccc     840
ttaaaagact gaacgctttt aaaatcggct cgcataaaat ggaagaattt agggataaac    900
aagggcgttt gtgggtagat gacagcaaag ccacaaacat tgatgccacc ttgcaagccc   960 taaaaaccctt taaaaaccaa aaaatccatt tgattttagg gggcgatatt aaagggtca    1020 atttaacccc ccttttttgaa gaatttaaaa atcatgaaat aagcctttat gccataggat   1080
caagcgcttt tattatccaa tccttagcat tagaatttaa tgtttcttgt caggtttgtt   1140
tggagttaga aaaagcggtt caagaaatta aaagcgtttt atcgcaaaat gaattgcttt   1200
tgctttcacc cagcgcagcc agtttggatc aattttcttc gtataaagaa aggggtgaaa   1260
```

-continued

```
gatttaaagc gtttgtttta aaagattaaa gcacatgcac cacttggtct aattgtgaaa    1320
ttttttgaaa aatctcgttc cgttcttctt catttgaaac ttccatagaa acattaaagc    1380
tataaaattt agcgttttta gaagtgtttt ttaattccaa tttaaagggg cgttggtagg    1440
tttctaaaag ctcttttaac acgcttgtat ctttagtagt cataatcacc ctataatccc    1500
aaagacaagg gtaaataata gtgggttttc ctgaatcaga tggcattgaa cagctcctta    1560
aacactttag gaatggcaat agggctgtat gtagagcgat tgacaaagcc aaacttgatt    1620
tctgaagcaa agaccttaaa aggcttcata ggctctaaag aagcgttttg gatgcaataa    1680
atttcttgaa aaagcaccac aaaaaccttt cttaattctt taatttgcgt tcttatttct    1740
aagacctgcc caaggcttgc gggggtgaaa aaatccgctt tgatagagcg ataacaaac     1800 acgccttctt cattttctgg caagacattt tgtttaaaaa aaaactcgct cctagccctt    1860
tcgcaatatt tcaaataatt cgcatgatag accacgcctt cagagtcggt atcttcgtaa    1920
tataccctac agcgcattga ttcccct tac tcaaataatg aaattttctt gaattatac    1980 aactatgtaa cttaactata gtataatcta ggggcgttgc ttatatttt taggtatttt    2040 taaagtggtt tttgtggttt ttttcttaaa tcttaagatc tttaaagatt ttagaaaact   2100
aatacagcaa tagttggacg attaaagaca ttgctcttta atttaatca tttataagga    2160 gtttggtagt taagatatgg gtaatcattt ttctaaatta ggatttgttt tagccgcatt    2220
aggaagcgcg ataggtttag gcatatctg gcgattcccc tatatgaccg gggtgagtgg    2280 tggggtgct tttgtttat tgttttt att tttatcttta agcgttggcg cggcgatgtt    2340
tatcgctgaa atgctattag gacaaagcac gcaaaaaaat gtaacagaag ctt           2393
```

<210> SEQ ID NO 9
<211> LENGTH: 926
<212> TYPE: DNA
<213> ORGANISM: Helicobacter pylori

<400> SEQUENCE: 9

```
aagctttagt gcgagattcc aatttgattt ctgctaaagc ccaagcggtg cctattgttt      60
tgcaattgca tgcgctatac aatgaagaaa acaattacac gcaatacctt ttaagcgtga    120
tgctgccttg catgtggctt attttgattg cgattggcat gctcaatttc attcaaaaag    180
cctctaacat gcacgagctt ttaatcagta ttttagcgaa tatgtgcgtg tttagtttt     240 gggggatggg catggcgttt tattttaatc tcattggcat ggagggacat tatgcgcatt    300
tgtcattggt ctttttggcg gtcgttttaa tggcgctcat tatgagcggg tttgtggtgt    360
tggtttatgg cgtttcaaaa agcgttattg aaaccgctgg cgcaattggg gtctataccg    420
ctccaagttt tgcgtttgct ggggttactt acccgcaaaa taacatggaa attttggga    480 gttttggag ccattgcttg cctattagcc attttatgaa gttctttta caagaggcct     540 attataagac ggattttaca gagtctttaa attctctaat gccgcttgcg ttctttttaa    600 tcttttagt cttagggctt ttgattttt attttctttt taaaaaaggc aaggctagcg     660
catgaatttt tttaaaatcc ttttaatgga gttaagggct attgtttctc ataagggcgt    720
tttgttaatc cttataggcg cgcctttaat ctatggctta ttatacccct tgccttattt    780
aaaagacatc gtaacgcagc aaaaaatcgc ccctttgtaga tgaagacaat tccttctttt   840
ccaggcaatt agcttcatg gtgcaaagct ccaacgagtt agaaatcgct ttttttagcc     900
cctctatgct ggaagccaaa aagctt                                          926
```

-continued

```
<210> SEQ ID NO 10
<211> LENGTH: 1219
<212> TYPE: DNA
<213> ORGANISM: Helicobacter pylori

<400> SEQUENCE: 10
aagcttatgg ggtttatgaa agcagctatt tgcaagaagt ccctagagat caatttgaag      60
gcattgaatt ggaaaaaggc atgagcgttt ttgggcaaac tgaagaccac aaaaccattc     120
aagccactat caaagacttt agcagcacgc atgtgatggt ggattataac catccgttag     180
ccgggaaaac tttagcgttt cgtttcaagg ttttgggctt tagggaagtg agcgaagaag     240
aaattttagc ttcacaccat ggcggtggga caggttgctg tggcggtcat gggggtcatg     300
gcggaaagaa aggtgggggc tgtggttgct catgttcgca tgggtagtag ggtataggag     360
catttaaaag gcaaggtcat gaatagttct aatctcaaaa attggctgtt ccctaccatt     420 tgctttttt tgttttgtta tattttaatt tttttgatgt tttttatgtt taaaagtttg      480
caatcgcaat cttttggctc tgtggcagaa accggaaaaa aacccatcac caccaccaag     540
aaatttggta aggaattgca aaaacagatt tcaaagatcc attaactttt tttcttttt      600 gccgatactt gccgtaatgg aatgaatatc aaattaaagg attttacaat gatcaatgcc     660
gtttcttctc tttctccggt gcaatctgtg gggaattaca agcgtgtgga aaagaatgaa     720
aaagttgaaa atagcgaggc cgctcttgat agggtggctg aaatcaagca agctattgaa     780
aacaaccagt ataaaatcaa cttgcatgag acttctcaca aaatggcaca ggatttattg     840
gggataggct aagggtttta agggcttcat ttctaggggg ggttattctt gctgtcgttt     900 tgttttttcat taaatttttag tttctttatg ttttgagttt tttgctctct taaatagggc    960 gtgttttttgt tgcgtgttag gaatgattga ttgggaattt taacttttat ggatttttgt   1020
tctggtattg gtggaggccg tttgggcttg gagcaatgcc atttaaaatg cgtagggcat    1080
gcagaaatca atcatgaagc cattagaact tatgggattat tttttaaaga tacccataat    1140
tttggggatt tgatgcgaat caaccctaat gatttacccg attttgatgc gctcattagc    1200
gggtttcctt gtcaagctt                                                  1219
```

PROBES FOR DETECTING AND IDENTIFYING *HELICOBACTER PYLORI*

TECHNICAL FIELD

The present invention relates to probes useful for detecting and identifying *Helicobacter pylori*, the causative bacteria of the digestive diseases including gastritis, gastric ulcer, duodenal ulcer or the like.

BACKGROUND ART

Since Warren's group reported the existence of *Helicobacter pylori* [Former Name: *Campylobacter pylori*] in the human gastric mucosal (Warren J. R. et al., "Unidentified curved bacilli on gastric epithelium in active chronic gastritis", Lancet 1: 1273–1275 (1983)), numerous researches have been performed with regard to the biochemical properties thereof, in particular, the correlation between *Helicobacter pylori* and digestive diseases including gastric ulcer, duodenal ulcer or the like.

In view of the focus that *Helicobacter pylori* have been separated/detected at a high rate from the human gastric mucosa of the gastritis patients or the gastriculcer patients [e.g., there are reports that they were detected at a rate of 50–80% in the cases of chronic gastritis, superficial gastritis, atrophic gastritis, erosive gastritis or the like], and the symptom of these digestive diseases are alleviated with sterilization by administration of drugs, accordingly, the correlation between *Helicobacter pylori* and the digestive diseases were suggested.

*Helicobacter pylori* would not make an invasion upon mucosal cells, but stay on the epithelial mucosa surface and/or the intercellular space and grow (proliferate) thereat. Then, it is thought that PAS (Periodic Acid-Sciff) reaction positive layer in the gastric mucosa are thinned through growth of *Helicobacter pylori*, thereby, effects of mucin which protects mucosa are declined, and potency on defense factor of the gastric mucosa are also declined (T. Ito, "Recent findings on *Helicobacter pylori*", Medical Technology, 19 (10), pp. 892–893 (September 1991)).

Then, the mechanism was also reported that *Helicobacter pylori* arrive and stay in gastric mucosal epithelium, then ammonia were produced through degradation of urea in the stomach by urease from *Helicobacter pylori*, the ammonia so produced damage gastric mucosa and generate reverse diffusion of the hydrogen ion, and, tumors are thereby formed (Tsujii, M. et al., "Mechanism of gastric mucosal damage Induced by ammonia", Gastroenterology 107: pp. 1881–1888 (1992)).

In general, conventional diagnosis of *Helicobacter pylori*, which is correlative to the human digestive diseases, includes:

(1) Direct proof on presence of *Helicobacter pylori* in a part of mucosa [Smear, Tissue-Microscopy, Cultivation],
(2) Detection utilizing character of *Helicobacter pylori* including urease activities, and
(3) Seroimmunodiagnosis (T. Shirai et al., "Diagnosis on Presence of *Campylobacter pylori*", Saishin-Igaku, 44 (2), 284–288 (1989)).

Of the methods aforenoted, a method (cultivation method) for detecting *Helicobacter pylori* through micro-aerobic cultivation of biopsy sample on gastric mucosa is the most reliable and accurate method. But, this method usually needs about one hour for a cultivation to grow the bacteria, the longer time would therefore be necessary to obtain the test results.

Then, in consideration of urease productivity by *Helicobacter pylori*, a method for directly detecting urease in samples of gastric biopsy have also been utilized (T. Ito, "Special diagnosis for bacterial infection/4. *Campylobacter pylori*", Rinnshoui, 15 (supplement), pp. 367–369 (1989). However, since these are methods to test the biopsy samples with an endoscope, the methods need the skilled operation and the patients will suffer from the unbearable pain.

Further, since urea in the stomach are degraded into ammonia and $^{14}CO_2$, there is a diagnosis including evaluation of such $^{14}CO_2$ by a scintillation counter. But, this method also needs a skilled work to handle radioisotope.

DISCLOSURE OF INVENTION

In view of the aforenoted problems in the art, the present invention was established to develop technology for easily, specifically and effectively detect *Helicobacter pylori* without introducing into patient's body any medical instrument like an endoscope.

Then, the merit of the invention is directed to probes having specific reactivities to DNAs or RNAs of *Helicobacter pylori* which is the causative bacteria of the digestive diseases including gastritis, gastric ulcer, duodenal ulcer or the like, and to analysis of base sequences in the probes concerning the characteristic gene portion of *Helicobacter pylori*.

That is to say, DNAs of the subject bacteria, *Helicobacter pylori*, can significantly be detected by the specificity between the probes of the present invention and the bacteria DNAs, thereby, *Helicobacter pylori* can be detected/identified rapidly and exactly without cultivating/growing *Helicobacter pylori*.

Then, if primers are designed based on base-sequence information of these probes, *Helicobacter pylori* can be identified by amplifying DNAs with PCR techniques without performing any hybridization procedure.

When non-radioactive probes, for example, biotinylated probes are employed for hybridization, since such probes can be detected with an optical microscope in a conventional laboratory without facilities to handle radioisotype, thereby, a process for detecting bacteria can perform rapidly and simply.

BEST MODE FOR CARRYING OUT THE INVENTION

Although examples of the probes prepared from *Helicobacter pylori* according to the present invention are illustrated as follows, the present invention shall not be limited due to disclosures of Examples.

EXAMPLE 1

DNA Probes Prepared from *Helicobacter pylori*

(1) Preparation of DNA probes from *Helicobacter pylori*

Firstly, Skirrow medium containing the components listed in the following Table 1 was prepared.

TABLE 1

| | |
|---|---|
| Blucella broth (Difco Co.,) | 14 g |
| Distilled Water | 500 ml |
| Polymyxin B | 1250 Unit |
| Vancomycin | 5 mg |
| Tripetoprim | 2.5 mg |
| Horse Serum (Difco Co.,) | 50 ml |
| Agar | 5 g |

Then, clinically isolated *Helicobacter pylori* were cultured in said Blucella broth (Difco Co., ) and said Skirrow medium under micro-aerobic condition [mixed gas consisting of 2% hydrogen, 5% oxygen, 7% carbon dioxide, 86% nitrogen (respectively expressed as volume %); relative humidity 90%] at 37° C. for five days to separate and grow *Helicobacter pylori*.

After the cultivation, the cultured bacteria were collected. Then, they were applied to the modified method based on Saito-Miura methodology ("Preparation of transforming deoxyribonucleic acid by phenol treatment", Biochem, Biophys. Acta vol. 72, pp. 619–629 (1963)) employing proteinase K (Merck)-0.1% SDS and utilizing an isolation method for nucleic acid, and the genomic DNAs thereof were extracted. Extracted DNAs were completely digested with the restriction enzyme HindIII, and were randomly cloned into vector pGEM-3Z (Promega).

Eight probes comprising DNA fragments, which specifically react with *Helicobacter pylori*, were selected from the clones so obtained, and each of which was designated as probe HP-32, probe HP-34, probe HP-49, probe HP-55 (down), probe HP-55 (up), probe HP-60, probe HP-64 and probe HP-66 (SEQ ID NOS: 3–10, respectively).

(2) Study on Species-Specificity of DNA Probes Prepared from *Helicobacter pylori*

Reactivities between each probe selected in Example 1 (1) and DNAs from various causative strains of infectious diseases were tested according to the following method.

First of all, as subject strains for the test, the clinically isolated strains and the deposited strains listed respectively in Table 2 were collected. In Table 2, Human Genomic DNA is Human Genomic DNA obtained from the human leukocytes of single healthy adult male (30 years old), while the control is *Escherichia coli* K-12, JM109 strain having plasmid pGEM-3Z (Seikagaku Kogyo).

TABLE 2

| Strain No. | Strain Name | Source |
|---|---|---|
| 1 | Helicobacter pylori | ATCC 43629 |
| 2 | Helicobacter pylori | Clinical Isolates |
| 3 | Helicobacter cineadi | ATCC 35683 |
| 4 | Helicobacter fennelliae | ATCC 35684 |
| 5 | Helicobacter mustelae | ATCC 43772 |
| 6 | Campylobacter jejuni | CIP 702 |
| 7 | Campylobacter coli | CIP 7080 |
| 8 | Campylobacter fetus | CIP 5396 |
| 9 | Streptococcus aureus | ATCC 25923 |
| 10 | Streptococcus epidermidis | Clinical Isolates |
| 11 | Escherichia coli | ATCC 25922 |
| 12 | Klebsiella pneumoniae | Clinical Isolates |
| 13 | Streptococcus pneumoniae | NYSDH DP-2 |
| 14 | Pseudomonas aeruginosa | Clinical Isolates |
| 15 | Enterobacter cloacae | Clinical Isolates |
| 16 | Haemophilis influenzae | Clinical Isolates |
| 17 | Candida albicans | ATCC 48130 |
| 18 | Aspergillus fumigatus | TIMM 0063 |
| 19 | Cryptococcus neoformans | TIMM 0354 |
| 20 | Mucor spinosus | TIMM 1322 |
| 21 | Absidia corymbifera | TIMM 2435 |
| 22 | Human Genomic DNA | |
| 24 | Control (Escherichia coli K-12, JM109(pGEM-3Z)) | |

Abbreviation
ATCC; American Type Culture Collection (Maryland, USA)
NYSDH; New York State Department of Health (Albany, New York, USA)
CIP; Collection of the Institute Pasteur (Paris, FRANCE)
TIMM; Teikyo University Institute of Medical Mycology (Tokyo, JAPAN)

Chromosomal DNAs in each strain were extracted according to the method of Example 1 (1) for the species belonged to Helicobacter genus referred to in Table 2 and according to Saito-Miura methodology (supra) employing lytic enzymes (lysostaphyn (Sigma), lysozyme (Sigma), acetylmuramidase SG (Seikagaku Kogyo)] for the other strains.

Samples for dot-blot-hybridization were obtained by spotting certain amount (e.g., 0.1 $\mu$g/5 $\mu$l) of the extracted DNAs onto nylon filters (Pauldyne) and selecting alkaline-denatured DNAs.

Samples of Human Genomic DNA were prepared by applying the previously obtained human leukocytes to Saito-Miura methodology (supra).

On the other hand, the controls were prepared by applying *Escherichia coli* K-12, JM109, which have plasmid pGEM-3Z (Promega) and was employed previously for cloning the probes, to the preparing method of the plasmid DNA to be referred to in the following Example 2 (1).

Then, with regard to the each sample, in accordance with Maniatis's manual (T. Maniatis, et al., "Molecular Cloning (A Laboratory Manual)", Cold Spring Harbour Laboratory (1982)), overnight hybridization was performed, under the condition of 45% formamido (Merck), 5×SSC and 42° C., using DNA probes which were prepared from *Helicobacter pylori* and were labelled with Digoxigenin-11-dUTP (Boehringer Mannheim).

After the overnight hybridization, the samples were washed twice with 0.1×SSC, 0.1% SDS for 20 minutes at 55° C., then were color-developed and detected with Anti-Dig-ALP conjugates (Boehringer Mannheim), and hybridization-specificities thereon had been confirmed.

Figure 1:
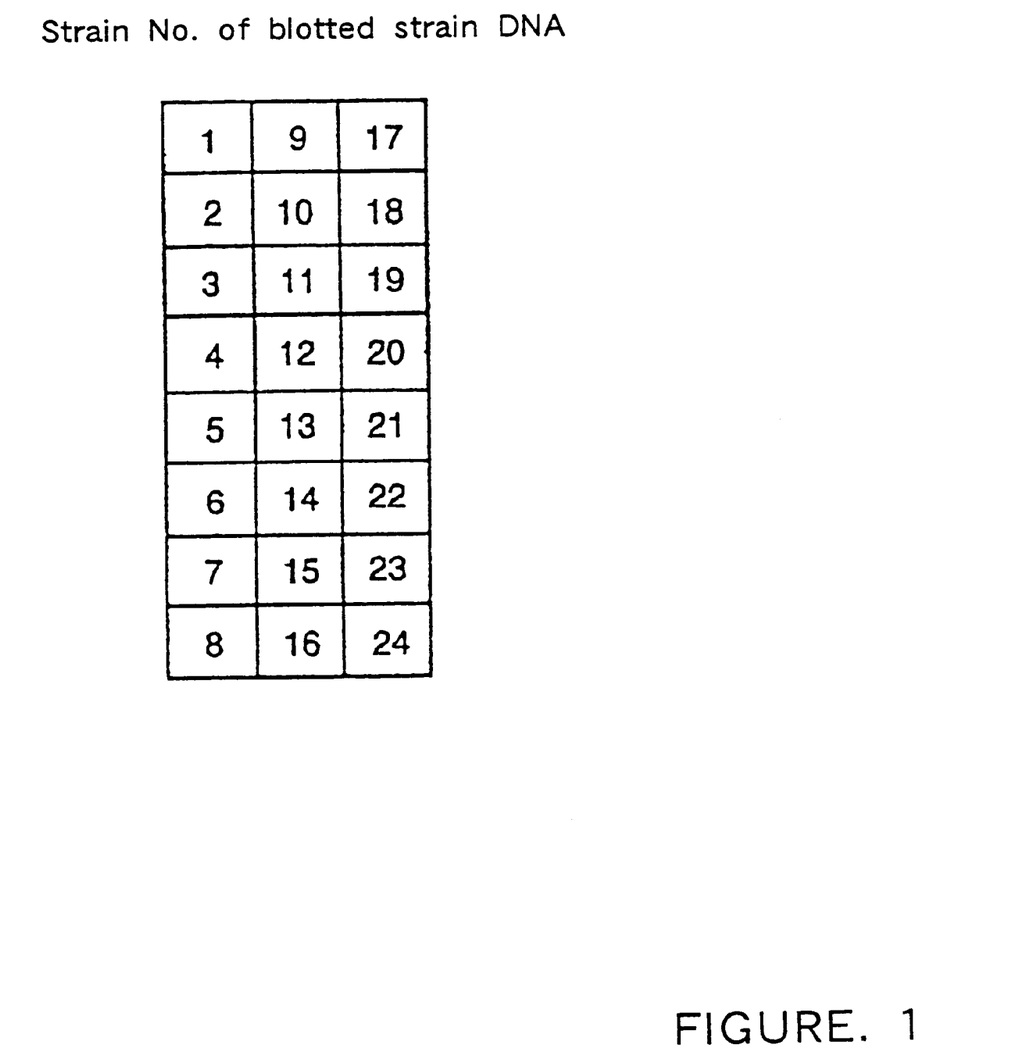
FIG. 1 is a view showing positional relation between well in the well-plate and the samples (blotted strain DNAs).
Figure 2:
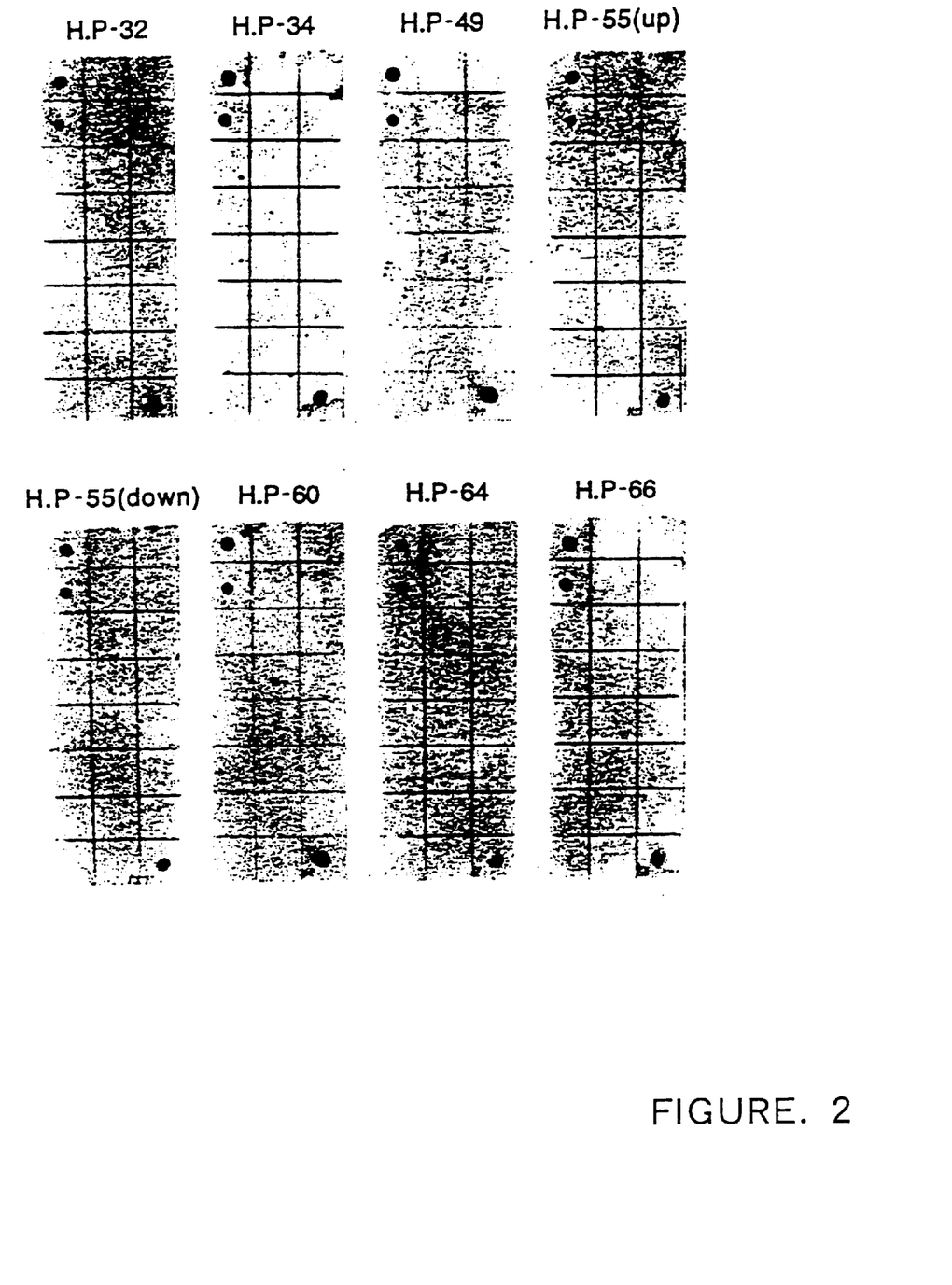
FIG. 2 is a view showing results of dot-hybridization on reactivities between the probes of the present invention and DNAs from various strains.

Experimental results on reactivities between each probe and DNAs from each clinically isolated strains are shown in FIG. 2. Then, positional relation between well in the well-plate and samples (blotted strain DNAs) to be blotted thereto were shown in FIG. 1. Namely, position numbers denoted in the schematic view of well-plate shown in FIG. 1 are corresponding to the sample (strain) numbers listed in Table 2.

Apparently from reaction results shown in FIG. 2, all of the tested probes have reacted only with DNAs from *Helicobacter pylori* (Strains Nos. 1 and 2), but not reacted (not hybridized) with any DNA from strains belonged to Helicobacter genus except from *Helicobacter pylori*, accordingly, their specificities have been confirmed.

EXAMPLE 2

Analysis of Base Sequence

Base sequences of DNA probes (total 8 probes), species-specificities of which have been confirmed in Example 1, were sequenced according to the following method.

(1) Preparation of Plasmid DNA

*Escherichia coli* K-12, JM109 comprising pGEM-3Z (Promega) incorporated thereinto the subcloned insert fragments (to be sequenced) was inoculated in 5 ml Luria-Bactani Medium (bacto-tryptone, 10 g/1 L; bacto-yeast extract, 5 g/1 L; NaCl, 10 g/1 L; pH 7.0 adjusted with 5 N NaOH) and was cultivated overnight.

Culture liquid was centrifuged (5,000 rpm, 5 min.) and the bacteria were collected. 100 μl solution of 50 mM glucose/25 mM Tris-HCl (pH 8.0)/10 mM EDTA containing 2.5 mg/ml lysozyme (Sigma) was added to the precipitates, and they were left at room temperature for five minutes. 0.2 M NaOH solution containing 1% sodium dodecyl sulfate (Sigma) was added to the suspension so obtained, and they were mixed. 150 μl of 5 M pottasium acetate solution (pH 4.8) was further added thereto, then they were mixed and were cooled with ice for 15 minutes.

Mix solution of water and phenol/chloroform ($CHCl_3$) (volume ratio of water:phenol/chloroform=1:1) was added to equivalent volume of supernatant obtained through the centrifugation (15,000 rpm, 15 min.) of the cooled solution, and they were mixed. Double volume of ethanol was added to the supernatant obtained from such mixed solution, then they were mixed, and precipitates were obtained through further centrifugation (12,000 rpm, 5 min.). These precipitates were dissolved in 100 μl solution of 10 mM Tris-HCl (pH 7.5)/0.1 mM EDTA, then 10 mg/ml RNaseA (Sigma) solution were further added thereto, and they were left at room temperature for 15 minutes.

300 μl of 0.1 M sodium acetate solution (pH 4.8) was added to such preparation, then, equivalent volume of mix solution consisting of water and phenol/chloroform ($CHCl_3$) (volume ratio of water:phenol/chloroform=1:1) was added thereto, and they were mixed. Double volume of ethanol was further added to the supernatant obtained from such mixed solution, and precipitates were obtained. DNA samples were prepared by drying these precipitates and dissolving them in 10 μl distilled water.

(2) Pretreatment for Sequencing

Pretreatment for sequencing was performed with Auto-Read™ Sequencing Kit (Pharmasia).

Concentration of DNA for a template was adjusted to 5–10 μg in 32 μl solution. 32 μl of template DNA solution was transferred to 1.5 ml mini-tube (Eppendolf), then 8 μl of 2 M NaOH solution was added thereto, and they were mixed gently. After light centrifugation, they were left at room temperature for 10 minutes.

7 μl of 3 M sodium acetate (pH 4.8) and 4 μl distilled water were added thereto, then 120 μl ethanol was further added, and they were mixed and were left for 15 minutes on dry ice. DNAs precipitated through 15-minutes centrifugation were collected, and supernatants were removed carefully. The precipitates so obtained were washed with 70% ethanol and were centrifuged for 10 minutes. Then, the supernatants were removed carefully again and the precipitates were dried under the reduced pressure.

Precipitates were dissolved in 10 μl distilled water, then 2 μl fluorescent primer [Fluorescent Primer, M13 Universal Primer; 5'-Fluorescein-d[CGACGTTGTAAAACGACGGCCAGT (SEQ ID NO: 1)]-3' (1.6 pmol/μl; 0.42 $A_{260}$ unit/ml); M13 Reverse Primer, 5'-Fluorescein-d[CAGGAAACAGCTATG AC(SEQ ID NO: 2)]-3' (2.1 pmol/μl; 0.42 $A_{260}$ unit/ml)] (0.42 $A_{260}$ unit/ml, 4~6 pmol) and 2 μl annealing buffer were added thereto, and they were mixed gently.

After light centrifugation, they were heated at 65° C. for 5 minutes, then were rapidly put under temperature of 37° C. and were kept the temperature for 10 minutes. Thereafter, they were left at room temperature for 10 minutes or more and were centrifuged lightly. Then, the samples were prepared by adding thereto 1 μl elongation buffer and 3 μl dimethyl sulfoxide.

Four mini-tubes have been marked with single symbol of "A", "C", "G" or "T", and, according to the written symbol, 2.5 μl of A Mix (ddATP dissolved together with dATP, dCTP, dGTP and dTTP), C Mix (ddCTP dissolved together with dATP, dCTP, dGTP and dTTP), G Mix (ddGTP dissolved together with dATP, dCTP, dGTP and dTTP), or T Mix (ddTTP dissolved together with dATP, dCTP, dGTP and dTTP) were poured into each tube. Each solution was preserved in ice until the use, and the solution was heated at 37° C. for one minute or more when it is actually used.

2 μl diluted T7DNA polymerase (Pharmacia; 6–8 units/2 μl) was added to each DNA sample, and was completely mixed by pipetting or gently mixing them. Immediately after completing the mixing, 4.5 μl of each of these mix solution were poured into prewarmed those four mix-solution respectively. Fresh tips were used at the time of pouring of these mix solution.

The solution was warmed for five minutes at 37° C., then 5 μl of termination solution attached to the previously noted AutoRead™ Sequencing Kit (Pharmacia) were poured into each reaction-solution. Fresh tips were also used at this pouring procedure.

The solution was warmed for two to three minutes at 90° C., and was immediately cooled on ice. 4–6 μl/lane of the solution was applied to the electrophoresis.

(3) Sequencing on Base Sequence

Base sequences of probes disclosed in Example 1 specific for *Helicobacter pylori* were sequenced with A. L. F. DNA Sequencer System (Pharmacia) under an electrophoresis condition of 45° C. for 6 hours.

As a result thereof, base sequences of probe HP-32 (SEQ ID NO:3), probe HP-34 (SEQ ID NO:4), probe HP-49 (SEQ ID NO:5), probe HP-55 (down) (SEQ ID NO:6), probe HP-55 (up) (SEQ ID NO:7), probe HP-60 (SEQ ID NO:8), probe HP-64 (SEQ ID NO:9) and probe SP-66 (SEQ ID NO:10) were clarified respectively.

INDUSTRIAL APPLICABILITY

According to the probes of the present invention, *Helicobacter pylori* can be directly detected and can rapidly/exactly be identified without using any invasive-medical instrument and growing the bacteria. That is to say, according to the diagnosis using the present probes, the detection rate would remarkably be improved, and the bacteria can be identified with single specimen, thereby, necessary time for diagnosis will be reduced to about one to two day(s). Therefore, an effective therapy will be able to plan in the early stage of the diseases and can immediately start.

Then, since the base sequences of the present probes, which are specific for DNAs of *Helicobacter pylori* involved closely with the human digestive diseases, have been clarified, these probes are able to prepare artifically. Further, causative bacteria DNAs in the clinical specimen can amplify with PCR techniques employing primers prepared by making use of a part of the analyzed base sequences, as a result thereof, *Helicobacter pylori* will rapidly be detected and the present probes can therefore be practically utilized in the diagnosis.

Further, by comparing base sequences of Genomic DNAs in the clinical specimen with those analyzed by the present invention, the causative bacteria species of digestive diseases will rapidly be identified.

As stated above, according to the present invention, contemplated probes specific for *Helicobacter pylori* are provided, and excellent utilities thereof are also expected as a guide factor for preparing PCR primers and as a standard sequence suitable for the comparison with Genomic DNAs in the clinical specimen. The present invention may further offer an effect to provide valuable hints for preparing and developing the other useful probes, which are specific for DNAs of *Helicobacter pylori* which is the causative bacteria of the digestive diseases. Then, since the base sequences disclosed in the present application were obtained by random-cloning the Genomic DNAs of clinically isolated strains, utilities of the base sequences of the present invention shall be extended to the complementary strands thereof.

It is naturally understood that DNAs of the wild strains contain the mutated portion. But, apparently from the disclosure of the illustrative Examples above, such mutated portions would not affect the specificity of the present probes as well as any utility for the clinical utility thereof (e.g., use of which to design PCR primers).

What is claimed is:

1. An isolated and purified probe consisting of a nucleotide sequence selected from the group consisting of SEQ ID NOS:3 through 10, wherein said probe specifically hybridizes with the DNA of *Helicobacter pylori*.

* * * * *